United States Patent [19]

Wiesehahn et al.

[11] Patent Number: 4,727,027

[45] Date of Patent: Feb. 23, 1988

[54] PHOTOCHEMICAL DECONTAMINATION TREATMENT OF WHOLE BLOOD OR BLOOD COMPONENTS

[75] Inventors: Gary P. Wiesehahn, Alameda; Richard P. Creagan, Alta Loma, both of Calif.

[73] Assignee: Diamond Scientific Co., Des Moines, Iowa

[21] Appl. No.: 785,356

[22] Filed: Oct. 7, 1985

Related U.S. Application Data

[63] Continuation-in-part of Ser. No. 928,841, Oct. 20, 1986, which is a continuation of Ser. No. 490,681, May 2, 1983, abandoned.

[51] Int. Cl.⁴ .................. C12N 13/00; C07K 13/00; A61K 39/00; C07G 7/00
[52] U.S. Cl. .................................. 435/173; 530/380; 530/381; 530/382; 530/385; 530/386; 530/387; 530/388; 530/392; 530/393; 530/347; 514/2; 514/6; 424/88; 424/89; 424/92; 424/101; 422/24; 422/28; 422/29; 426/234; 426/318
[58] Field of Search ............... 435/173, 183, 188, 236, 435/238, 269, 800, 814, 172.1; 260/112 R, 112 B, 121; 424/89, 90, 101, 88, 92; 514/2, 6, 8; 530/350, 363, 380–394, 412–414, 427

[56] References Cited

U.S. PATENT DOCUMENTS

| | | | |
|---|---|---|---|
| 4,124,598 | 11/1978 | Hearst et al. | 260/343.21 |
| 4,169,204 | 9/1979 | Hearst et al. | 546/270 |
| 4,321,919 | 3/1982 | Edelson | 128/214 R |
| 4,327,086 | 4/1982 | Fukushima et al. | 424/177 |
| 4,568,542 | 2/1986 | Kronenberg | 424/90 |
| 4,595,653 | 6/1986 | Kronenberg | 435/5 |

OTHER PUBLICATIONS deMol and van Henegouwen (1981) Photochem. Photobiol. 33:815–819.
deMol et al. (1981) Photochem. Photobiol. 34:661–666.
Joshi and Pathak (1983) Biochem. Biophys. Res. Comm., 112:638–646.
Grossweiner (1982) NCI Monograph No. 66, 47–54.
Rodighiero and Dall'Acqua (1982), NCI Monograph No. 66, 31–40.
deMol et al. (1981) 95:74462k, p. 74467 Chem. Interactions.
Hyde and Hearst (1978) Biochemistry 17:1251–1257.
Hanson et al. (1978), J. Gen. Virol. 40:345–358.
Swanstrom et al. (1981), Virol. 113:613–622.
Redfield et al. (1981), Infec. and Immun. 32:1216–1226.
Hanson "Inactivation of Viruses for Use as Vaccines . . . . Med. Virol., II, de la Maza & Peterson, eds.
Cremer et al., (1982) J. Clin, Microbiol., 15:815–823.
Veronese, F. M., et al., (1981), Photochem. Photobiol. 34:351.
Veronese et al. (1982), Photochem. Photobiol. 36:25.
Singh and Vadasz (1978) Photochem. Photobiol. 28:539–545.
Musajo et al, *Experentia*, vol. XXI, pp. 22–24, "Photosensitizing Furocovmanhs–Interaction with DNA and Photoinactivation of DNA Containing Viruses".

*Primary Examiner*—Thomas G. Wiseman
*Assistant Examiner*—Robin Lyn Tieskin
*Attorney, Agent, or Firm*—Zarley McKee, Thomte, Voorhees & Sease

[57] ABSTRACT

Biological compositions are decontaminated by treatment with furocoumarin derivatives and irradiation under particular conditions in which the proteins retain their original physiological activities and any pathogenic microorganisms and polynucleotide fragments thereof are rendered inactive. It has been found that reduction of the amount of dissolved oxygen in the treatment solution substantially inhibits denaturation of the proteins.

22 Claims, No Drawings

PHOTOCHEMICAL DECONTAMINATION TREATMENT OF WHOLE BLOOD OR BLOOD COMPONENTS

This application is a continuation-in-part of application Ser. No. 928,841, filed Oct. 20, 1986, which is a continuation of application Ser. No. 490,681, filed on May 2, 1983 now abandoned.

BACKGROUND OF THE INVENTION

1. Field of the Invention

Recipients of blood and blood components risk acquiring infections from pathogenic microorganisms, either pre-existing in the blood at the time of collection or transmitted to the blood product during manipulation. Medical personnel who are in contact with collected human blood or clinical samples also have a significant chance of being exposed to potentially lethal blood-borne or sample-borne organisms. Blood components today are obtained from blood donors and frequently involve pooled lots, where one or more of the donors may be harboring a viral, bacterial or other infection. Since the blood or blood components are required to provide physiological functions in a mammalian host, normally a human host, these functions must not be impaired by the decontamination treatment of the biological composition. In addition, the blood or blood components may not be modified in such a way as to make them immunogenic which could result in an adverse immune response. Finally, any treatment should not leave residues or products detrimental to the health of the host or such residues or products should be readily removable.

2. Description of the Prior Art

U.S. Pat. No. 4,327,086 describes a method for heat treating an aqueous solution containing human blood coagulation factor XIII. U.S. Pat. No. 4,321,919 proposes extracorporeal treatment of human blood with 8-methoxypsoralen (8-MOP) and ultraviolet light. Hyde and Hearst, Biochemistry (1978) 17: 1251-1257, describe the binding of two psoralen derivatives to DNA and chromatin. Musajo et al., Experientia (1965) XXI, 22-24, describe photo-inactivation of DNA-containing viruses with photosensitizing furocoumarins. See also, Hanson et al. (1978) J. Gen. Virol. 40: 345-358; Swanstrom et al. (1981) Virol. 113: 613-622; Redfield et al. (1981) Infec. and Immun. 32: 1216-1226; Hanson (1983) "Inactivation of Viruses for Use as Vaccines and Immunodiagnostic Reagents" in Medical Virology II, de al Maza and Peterson, eds., and Cremer et al. (1982) J. Clin. Microbiol. 15: 815-823, each of which describe viral inactivation by exposure to ultraviolet radiation in the presence of furocoumarins.

Some data showing substantial impairment of the biological function of certain enzyme proteins using furocoumarins are published in the scientific literature (see for example, Veronese, F. M. et al., Photochem. Photobiol. 34: 351 (1981); Veronese, F. M. et al., Photochem. Photobiol. 36: 25 (1982)). Singh and Vadasz (1978) Photochem. Photobiol. 28: 539-545 attribute the photoinactivation of E. coli ribosomes by ultraviolet radiation in the presence of furocoumarins to the presence of singlet oxygen.

SUMMARY OF THE INVENTION

Methods and compositions are provided for the decontamination of biological compositions, such as blood and blood products, by inactivating microorganisms and polynucleotide fragments thereof capable of causing a pathological effect in mammalian hosts. The biological compositions are decontaminated by treatment with furocoumarins and long wavelength ultraviolet (UVA) light under conditions which limit the availability of oxygen and other reactive species. It has been found that such conditions allow for inactivation of even recalcitrant viral pathogens without degrading biologically active proteins, such as Factor VIII, which are present in the composition.

DESCRIPTION OF THE SPECIFIC EMBODIMENTS

In accordance with the subject invention, biological compositions which may harbor microorganisms capable of causing harmful physiological effects in a host are combined with furocoumarin compositions and treated with UVA light under predetermined conditions, whereby the microorganisms and polynucleotide fragments thereof are inactivated while the physiological activities of non-nucleic acid components of the compositions are retained. The treatment conditions are selected to minimize the likelihood that biologically active non-nucleic acid components of the compositions, such as proteins, are degraded. In particular, precautions are taken to reduce the level of dissolved oxygen and other reactive species in the composition during exposure to the ultraviolet light. As used hereinafter and in the claims, the term "microorganisms" should be understood to mean (1) prokaryotic, eukaryotic and viral microorganisms containing nucleic acids (either DNA or RNA), and
(2) nucleic acid genomes or sub-genomic fragments from microorganisms.

Various biological compositions may be decontaminated by the methods of the present invention, particularly aqueous compositions containing biologically active proteins derived from blood or blood components. Whole blood, packed red cells, platelets, and plasma (fresh or fresh frozen plasma) are exemplary of such compositions. Blood components of particular interest include plasma protein portion, antihemophilic factor (AHF, Factor VIII); Factor IX and Factor IX complex (Factors II, VII, IX and X); fibrinogens, Factor XIII, prothrombin and thrombin (Factor II and IIa); immunoglobulins (e.g. IgA, IgD, IgE, IgG and IgM and fragments thereof e.g. Fab, F(ab')$_2$, and Fc); hyper-immune globulins as used against tetanus and hepatitis B; cryoprecipitate; albumin; interferons; lymphokines; transfer factors; etc. Other biological compositions include vaccines, recombinant DNA produced proteins, oligopeptide ligands, etc. The protein concentration in the aqueous biological compositions will generally range from about 1 $\mu$g/ml to 500 mg/ml, more usually from about 1 mg/ml to 100 mg/ml. The pH will normally be close to physiologic pH ($\sim$7.4), generally in the range of about 6 to 9, more usually about 7. Other components may be present in the compositions, such as salts, additives, buffers, stabilizers, or the like. These components will be conventional components, which will be added for specific functions.

Furocoumarins useful for inactivation include psoralen and derivatives, where the substituents will be: alkyl, particularly of from 1 to 3 carbon atoms, e.g. methyl; alkoxy, particularly of from 1 to 3 carbon atoms, e.g. methoxy; and substituted alkyl, of 1 to 6, more usually 1 to 3 carbon atoms having from 1 to 2 heteroatoms, which will be oxy, particularly hydroxy or alkoxy of from 1 to 3 carbon atoms, e.g. hydroxymethyl and methoxymethyl, or amino, including mono- and dialkyl amino having a total of from 1 to 6 carbon atoms, e.g. aminomethyl. There will be from 1 to 5, usually 2 to 4 substituents, which will normally be at the 4, 5, 8, 4' and 5'-positions, particularly at the 4'-position. Illustrative compounds include 5-methoxypsoralen, 8-methoxypsoralen (8-MOP), 4,5',8-trimethylpsoralen (TMP), 4'-hydroxymethyl-4,5',8-trimethylpsoralen (HMT), 4'-aminomethyl-4,5',8-trimethylpsoralen (AMT), 4-methylpsoralen, 4,4'-dimethylpsoralen, 4,5'-dimethylpsoralen, 4',8-dimethylpsoralen, and 4'-methoxymethyl-4,5',8-trimethylpsoralen.

When employing furocoumarins with limited aqueous solubility, typically below about 50 $\mu g/ml$, it has been found useful to add an organic solvent, such as dimethyl sulfoxide (DMSO), ethanol, glycerol, polyethylene glycol (PEG), or polypropylene glycol to the aqueous treatment solution. Such furocoumarins having limited solubility include 8-MOP, TMP, and psoralen. By adding small amounts of such organic solvents to the aqueous composition, typically in the range from about 1 to 25% by weight, more typically from about 2 to 10% by weight, the solubility of the furocoumarin can be increased to about 200 $\mu g/ml$, or higher. Such increased furocoumarin concentration may permit the use of shorter irradiation times. Also, inactivation of particularly recalcitrant microorganisms may be facilitated without having to increase the length or intensity of ultraviolet exposure, and the addition of an organic solvent may be necessary for inactivation of some viruses with particular furocoumarins. The ability to employ less rigorous inactivation conditions is of great benefit in preserving the biologic activity of blood proteins during decontamination.

At times, it may be desirable to employ organic solvents, particularly DMSO, with all furocoumarins regardless of solubility. For some microorganisms, particularly viruses having tight capsids, the addition of the organic solvent may increase the permeability of the outer coat or membrane of the microorganism. Such increase in permeability would facilitate penetration by the furocoumarins and enhances the inactivation of the microorganism.

The subject furocoumarins are active with a wide variety of pathogenic microorganisms, viruses, and polynucleotide fragments thereof, DNA or RNA, whether single stranded or double stranded. Illustrative viruses include: adenovirus, arenavirus, bacteriophage, bunyavirus, hepatitis viruses, including types A, B and non-A, non-B (also designated type C), herpesvirus, retroviruses such as human T-lymphtropic viruses (HTLV), including HTLV types I, II and III, orthomyxovirus, papovavirus, paramyxovirus, picornavirus, poxvirus, reovirus, rhabdovirus, and togavirus. Additional pathogenic microorganisms include bacteria, chlamydia, mycoplasma, protozoa, rickettsia and other unicellular microorganisms. This inactivation method will also be effective against uncharacterized infectious agents which contain nucleic acids, either DNA or RNA.

The furocoumarins may be used individually or in combination. Each of the furocoumarins may be present in amounts ranging from about 0.01 $\mu g/ml$ to 1 mg/ml, preferably from about 0.5 $\mu g/ml$ to 100 $\mu g/ml$, there not being less than about 1 $\mu g/ml$ nor more than about 1 mg/ml of furocoumarins.

The furocoumarins may be added to the biological composition by any convenient means in a manner substantially assuring the uniform distribution of the furocoumarins in the composition. Such addition may be made in a single dose, in a series of doses over time, or continuously during the entire treatment period or a portion thereof. The composition may be irradiated under conditions ensuring that the entire composition is exposed to sufficient irradiation, so that the furocoumarins may react with any polynucleotide present to inactivate the polynucleotide. Depending upon the nature of the composition, particularly its opacity, as in the case of blood, the depth of the solution subject to irradiation will vary widely. Usually, the depth will be not less than about 0.025 millimeter, but may be a centimeter or more. With whole blood, the depth will generally range from about 0.025 millimeter to 2.5 millimeters. The light which is employed will generally have a wavelength in the range of about 300 nm to 400 nm. Usually, an ultraviolet light source will be employed together with a filter for removing UVB light. The intensity will generally range from about 0.1 mW/cm$^2$ to about 5 W/cm$^2$, although in some cases it may be much higher. The medium being irradiated may be irradiated while still, stirred or circulated, and may either be continuously irradiated or be subject to alternating periods of irradiation and non-irradiation. The circulation may be in a closed loop system or it may be in a single pass system ensuring that all of the sample has been exposed to irradiation. The total time for irradiation will vary depending upon the nature of the sample, the furocoumarin derivative used, the intensity and spectral output of the light source and the nature of the polynucleotides which may be present. The time of irradiation necessary for inactivation will be inversely proportional to the light intensity. Usually, the time will be at least 1 min. and not more than about 20 hrs., more usually from about 15 mins. to about 2 hrs. When circulating the solution, the rate of flow will generally be in the range of about 0.1 ml/min to 50 liters/min.

In order to inhibit denaturation of biologically active proteins, it is desirable to reduce the availability of dissolved oxygen and other reactive species in the biological composition before or during the exposure to ultraviolet radiation. A variety of steps to reduce the oxygen availability may be taken, either individually or in combination. Oxygen scavengers, such as ascorbate, glutathione, sodium thionate, and the like, may be added which combine with singlet oxygen and other reactive oxygen species to prevent reaction with the proteins. Physiologically acceptable proteins, such as human or bovine serum albumin (BSA), and the like, may also be added. Such large proteins act both to bind metals which catalyze reactions involving oxygen as well as by preferentially binding the oxygen and other reactive radicals. The biological composition may also be flushed with inert or less reactive gases, such as hydrogen, helium, neon, carbon dioxide, nitrogen, argon, and the like, to reduce the concentration of oxygen and other dissolved gases in the biological composition by equilibrium exchange (mass transfer) with the flushing gas. Flushing may be accomplished by passing the inert gas over or through the biological composition, for a predetermined minimum amount of time, usually at least 30 minutes, more usually at least one hour, prior to exposure to the ultraviolet radiation.

The concentration of dissolved oxygen may also be reduced through the use of enzyme systems either in solution or immobilized on a solid substrate. Suitable enzyme systems include glucose oxidase or catalase in the presence of glucose and ascorbic acid oxidase in the presence of ascorbate. Such enzyme systems may be employed alone or together with the other methods for oxygen reduction discussed above.

To further inhibit denaturation of the biologically active proteins, the temperature of the biological composition should be maintained below about 60° C., preferably below 40° C., more preferably in the range from $-10°$ C. to 30° C., during exposure to the ultraviolet radiation.

It may be desirable to remove the unexpended furocoumarin and/or its photobreakdown products from the irradiation mixture. This can be readily accomplished by a variety of conventional separation techniques, such as dialysis across an appropriately sized membrane or through an appropriately sized hollow fiber system after completion of the irradiation. It may be desirable in certain applications to remove bound or unbound furocoumarins using affinity methods (e.g., magnetic beads) or using antibodies, including monoclonal antibodies, either in solution or attached to a substrate. Enzymes, either in solution or attached to a substrate, could be used to convert the furocoumarins to nontoxic unreactive products. Alternatively, desirable components such as factor VIII could be removed by precipitation or affinity methods by leaving the furocoumarins in solution.

The following examples are offered by way of illustration and not by way of limitation.

EXPERIMENTAL

The following experiments were performed in order to demonstrate the ability of psoralen photoreaction to destroy microbial contaminants contained in whole blood and blood products without destroying the biological activity of blood proteins.

Since whole blood exhibits very high optical density for longwave UV light (320 nm to 380 nm), the blood was irradiated through a suitably short optical path length. In Example I, blood was pumped through polyethylene capillary tubing of 0.875 millimeter inside diameter. The tubing was coiled around a 1.27 centimeter diameter tube and immersed in water which was maintained at 18° C. The blood was continuously circulated through the tubing by means of a peristaltic pump. The blood required approximately 2.5 minutes for a complete cycle through the capillary tubing and was in the light beam for approximately 20% of the stated irradiation time. The light source was a low pressure mercury lamp filtered through a cobalt glass filter. The filter transmits light of approximately 320 nm–380 nm, with peak transmittance at 360 nm. The incident intensity at the sample was approximately 40 mW/cm². The apparatus employed for Examples II through XI consisted of an upper and lower bank of lamps emitting longwave ultraviolet light (e.g. GE F20T12 BLB bulbs, 320–400 nm). Samples were placed on plate glass between the light sources. Irradiation times and intensities were as described for each Example.

EXAMPLE I

Inactivation of feline rhinotracheitis

Feline rhinotracheitis virus, a member of the herpesvirus family, was added to heparinized whole rabbit blood in an amount that would give a final concentration of approximately $2 \times 10^7$ PFU/ml. 4'-hydroxymethyl-4,5',8-trimethylpsoralen (HMT) was added to a portion of the rabbit blood and aliquots were irradiated for various periods of time. To test for remaining live virus, duplicate plaque assays were performed using cultured feline cells (Fc3Tg) (ATCC CCL 176), with a methylcellulose overlay. Virus titers were obtained as the arithmetical mean of viral plaques observed in duplicate assays cultures 72 hours after exposure to test samples.

The blood aliquot that received HMT only and no irradiation gave a titer of $5.3 \times 10^6$ PFU/ml. The aliquot that received HMT and five minutes of irradiation exhibited a titer of $4.5 \times 10^6$ PFU/ml. In the aliquot that received psoralen plus one hour of irradiation there was not detectable live virus remaining. The sensitivity of this assay should have permitted detection of residual virus at titers $\geq 1.0 \times 10^1$ PFU/ml. A blood sample which had received HMT and one hour of irradiation also showed no apparent damage to the red blood cells as judged by phase contrast microscope analysis and by absence of visible hemolysis. These data therefore demonstrate that high virus titers present in whole blood can be inactivated by psoralen plus light treatment which leaves the red cell component of the blood intact.

EXAMPLE II

Protective effect of inert gas flushing on Factor VIII activity

Eight samples of pooled normal plasma were prepared and treated as follows. Samples 5-8 were continuously flushed with argon. AMT (20 μg/ml) and TMP (5 μg/ml) were added to samples 2, 4, 6, and 8. Samples 3, 4, 7, and 8 were exposed to UVA radiation (4.2 mW/cm², 320-400 nm). Factor VIII activity was determined for each sample after six hours of such treatment. The results are set forth in Table 1.

TABLE 1

| Sample | Argon | UVA | Drugs | FVIII Activity units/ml | % Retained |
|---|---|---|---|---|---|
| 1 | 0 | 0 | 0 | 0.86 | Control |
| 2 | 0 | 0 | + | 0.84 | 98 |
| 3 | 0 | + | 0 | 0.58 | 67 |
| 4 | 0 | + | + | 0.10 | 12 |
| 5 | + | 0 | 0 | 0.75 | 87 |
| 6 | + | 0 | + | 0.64 | 74 |
| 7 | + | + | 0 | 0.58 | 67 |
| 8 | + | + | + | 0.45 | 52 |

These results demonstrate that argon flushing to reduce the level of dissolved oxygen in the treatment solution substantially enhances the retention of Factor VIII activity.

EXAMPLE III

Protective effect of ascorbate on Factor VIII activity

Three samples of Factor VIII concentrate were prepared with 3% BSA added. Test samples 2 and 3 were flushed with argon prior to UVA exposure. Nothing further was added to the first sample. AMT (180 μg/ml) was added to the second and third samples, while 5 mM ascorbate was added to the third sample only. The second and third samples were exposed to UVA (4.2 mW/cm², 320-400 nm) radiation for the four hour period, while the first sample was kept in the dark (control). Factor VIII activity of all samples was measured after the four hour test period and the retained activity was determined. The results are summarized in Table 2.

TABLE 2

| Sample | UVA | AMT | Ascorbate | FVIII Activity units/ml |
|---|---|---|---|---|
| 1 | 0 | 0 | 0 | 0.81 |
| 2 | + | + | 0 | 0.38 |
| 3 | + | + | + | 0.59 |

These results demonstrate that the addition of ascorbate to the treatment solution substantially enhances the retention of Factor VIII activity in samples treated with psoralens and exposed to ultraviolet radiation.

EXAMPLE IV

Protective effect of BSA on Factor VIII activity

Six samples of Factor VIII concentrate were flushed with argon and then exposed for three hours to UVA radiation (4.2 mW/cm$^2$, 320–400 nm). Selected amounts of AMT and/or BSA were added to certain samples prior to irradiation. Factor VIII activity was measured before and after irradiation, and the percentage of retained activity determined. The results are set forth in Table 3.

TABLE 3

| Sample | AMT(μg/ml) | BSA(%) | Retained F VIII Activity (%) |
|---|---|---|---|
| 1 | 0 | 0 | 88 |
| 2 | 0 | 10 | 110 |
| 3 | 30 | 1 | 77 |
| 4 | 30 | 5 | 98 |
| 5 | 30 | 10 | 86 |
| 6 | 60 | 10 | 84 |

These results demonstrate that BSA enhances the retention of Factor VIII activity when exposed to UVA radiation, both in the presence and absence of AMT.

EXAMPLE V

Inactivation of Mycoplasma species Acholeplasma laidlawii with 8-MOP

Culture: Six days old and approximately 10$^7$ cells/ml.

Irradiation: Irradiated samples were exposed to UVA (approximately 4.2 mW/cm$^2$) for three exposure periods of two hours each. Samples were transferred to a new vessel for each period of UVA treatment.

Furocoumarin: 8 methoxypsoralen (8-MOP) in DMSO was used at the concentrations given in Table 4. After each two hour period of irradiation, a fresh aliquot of furocoumarin was added to restore the minimal drug concentration to the level indicated in Table 4.

Additives: Additional DMSO and/or sodium ascorbate (ASC) were added to samples as indicated in Table 4.

Assay: Residual live mycoplasma were assayed using the standard microbiological culture tests prescribed by the U.S. Department of Agriculture in 9CFR part 113.28.

TABLE 4

| Treatment of Samples | Mycoplasma Growth Test | | % DMSO final (v/v) |
|---|---|---|---|
| | Direct Plating | Bulk Broth | |
| UVA only | + | + | 0 |
| DMSO (6% v/v) | + | + | 6 |
| ASC (10 mM) | + | + | 0 |
| UVA + ASC | + | + | 0 |
| UVA + DMSO + ASC | + | + | 6 |
| ASC + DMSO | + | + | 6 |
| UVA + ASC + 8-MOP (100 μg/ml) | − | + | 2.3 |
| UVA + DMSO + ASC + 8-MOP (100 μg/ml) | − | + | 8.2 |
| UVA + ASC + 8-MOP (200 μg/ml) | − | − | 4.6 |
| UVA + DMSO + ASC + 8-MOP (200 μg/ml) | − | − | 10.6 |

+ = growth
− = no growth

These results demonstrate that the decontamination method of the present invention is useful for the inactivation of bacterial species.

EXAMPLE IV

Inactivation of Mycoplasma species Mycoplasma orale with AMT and TMP without additives Culture: Seven days old and approximately 2.9 × 10$^6$ cells/ml.

Irradiation: Same as for Example V except irradiated samples were only exposed for one treatment period of the duration indicated in Table 5.

Furocoumarins: 4'aminomethyl-4,5',8-trimethlylpsoralen (AMT) 4,5',8-trimethylpsoralen (TMP)

Additives: None

Assay: Same as for Example V.

TABLE 5

| Treatment of Samples | Mycoplasma Growth Test | |
|---|---|---|
| | Direct Plating | Bulk Broth |
| No treatment | + | + |
| UVA (1 hour) | + | ND |
| UVA (3 hours) | − | ND |
| AMT (30 μg/ml) | + | ND |
| AMT (30 μg/ml) + UVA (1 hour) | − | + |
| AMT (30 μg/ml) + UVA (3 hours) | − | − |
| TMP (7.5 μg/ml) + UVA (1 hour) | − | − |

ND = not done, + = growth, − = no growth

These results further confirm the efficacy of the present invention in inactivating bacterial species.

EXAMPLE VII

Inactivation of vesicular stomatitis virus and retention of Factor VIII activity Treatment samples comprising vesicular stomatitis virus (3.3 × 10$^8$ pfu/ml) were prepared in PBS-diluted AHF concentrate. The VSV was inactivated in two samples by the addition of AMT (180 μg/ml), 1% BSA, 10 mM ascorbate, and exposure to UVA (6.4 mW/cm$^2$, 320–400 nm) for approximately nine hours. The samples were continuously flushed with argon. Inactivation was confirmed by plaque assay on LM(TK$^-$) mouse cells and by injection of 20 μl into suckling mouse brains. The mouse brain assay will detect 10 pfu/ml. Both samples were shown to be non-infective. Factor VIII activity was monitored in the treated samples as well as a control sample which was not irradiated using a modified APTT assay. The effect on the Factor VIII activity is shown in Table 6.

TABLE 6

| Sample | Elapsed Time | VSV (pfu/ml) | FVIII Activity (U/ml) |
|---|---|---|---|
| 1 | 0 | $10^8$ | 7.2 |
|   | 9 | 0 | 6.6 |
| 2 | 0 | $10^8$ | 6.25 |
|   | 2 | 0 | ND |
|   | 9 | 0 | 5.6 |
| CONTROL | 0 | $10^8$ | * |
|   | 9 | $10^8$ | * |

ND: Not done
*No significant loss of activity

These results demonstrate that a virally infected biological composition may be decontaminated by the method of the present invention without substantial loss of biological activity of a biologically-active protein.

EXPERIMENT VIII

Inactivation of non-A, non-B hepatitis virus

A study was undertaken to evaluate the effects of furocoumarin and UVA on the virus which causes non-A, non-B hepatitis. This virus is believed to be the major cause of post-transfusion hepatitis in the United States. The only suitable animal model for this virus is the chimpanzee model. Samples of non-A, non-B hepatitis virus were inactivated, as described below, and injected into chimpanzees. The samples were injected intravenously into chimpanzees anesthetized with ketamine. These animals were naive with respect to non-A, non-B hepatitis, had been followed for an extended period with normal liver enzymes (SGPT, SGOT), and had at least two normal liver biopsies examined by light and electron microscopy in the two month period prior to inoculation. During the trial, liver enzymes were checked weekly and periodic liver biopsies were done. Results through 26 weeks post-inoculation indicate that there were no significant liver enzyme elevations, and liver biopsies were negative.

Inactivation was as follows. Four coded samples were obtained which contained from 100 to 100,000 chimpanzee infectious doses (CID$_{50}$) of the Hutchinson strain of non-A, non-B hepatitis virus in 1.0 ml of fetal calf serum. These samples were treated under code as follows. Each sample was diluted with phosphate buffered saline to a total of 10.0 ml containing a final concentration of the following:
1% Bovine serum albumin
5 mM Sodium ascorbate
20 μg/ml AMT
0.5 μg/ml TMP Each 10.0 ml sample was added to a T-75 flask (Corning) prerinsed with 5% BSA, flushed with argon and incubated in the dark overnight at room temperature (21° C.). The flasks were then irradiated at an average of 5.0 mW/cm$^2$ under black light bulbs emitting UVA light (G.E. BLB F20T12). At 1 hour intervals an additional 20 μg/ml AMT and 0.5 μg/ml TMP were added and the flasks reflushed with argon. At three hour intervals the samples were transferred to fresh BSA-rinsed flasks.

Parallel flasks with $10^8$ pfu/ml vesicular stomatitis virus (VSV) in place of the non-A, non-B virus (inactivation control) were prepared and irradiated as above. Samples were taken for testing at 0, 1, 3 and 6 hours. Parallel flasks with 10% factor VIII concentrate (Koate, Cutter Biological) were prepared and irradiated as above. Samples were taken at time 0 and at 3 hour intervals and frozen at −80° C. After 9 hours the experiment was stopped temporarily and resumed the next morning. Samples were kept at room temperature (21° C.) during this time. Conditions for the second 9 hours were the same as for the first 9 hours except that a second parallel VSV sample was prepared with $10^8$ VSV/ml. Aliquots from this second VSV sample were removed at 2, 4, and 5 hours for subsequent assays. The VSV aliquots were assayed for residual viral activity by plaque assay on LM(TK$^-$) cells and by injection into suckling mouse brains. Factor VIII activity in the concentrate samples was determined by a one stage clotting test.

At the conclusion of the second 9 hours, the samples containing non-A, non-B hepatitis were sent under code to Southwest Foundation for Research and Education (SFRE), now known as Southwest Foundation for Biomedical Research (SFBR), for inoculation of chimpanzees. Chimpanzees received the following doses of inactivated non-A, non-B hepatitis virus:

| Chimp No. | Inactivated Virus (CID$_{50}$) |
|---|---|
| 72 | 100 |
| 83 | 1,000 |
| 80 | 10,000 |
| 97 | 100,000 |

All four chimps remained negative for non-A, non-B hepatitis infection during six months of clinical observation. Following the six month observation period, chimp no. 97 who had received the highest dose (approx. 100,000 CID$_{50}$) of inactivated non-A, non-B hepatitis virus, was inoculated with approximately 33 CID$_{50}$ live virus. This challenge dose was prepared from a reserved aliquot of the original sera from which the inactivated viruses had been obtained. Chimp no. 97 developed symptoms of infection 10 weeks after inoculation, thus demonstrating the chimp's susceptibility to the virus. This experiment demonstrated that the inactivation procedures used were capable of killing at least $10^{3.5}$ CID$_{50}$ virus.

In the parallel experiments, VSV at $3.4 \times 10^8$ pfu/ml (average of 2 experiments) was reduced to non-detectable levels in plaque assays after two hours of the inactivation procedure. No residual infectivity was detected by the more sensitive suckling mouse brain assay in inocula subjected to four hours of inactivation (Table 7).

TABLE 7

| Fucoumarins/UVA (hours) | VSV Plaques (pfu/ml) | Suckling Mice (days to death) |
|---|---|---|
| 0 | $3.4 \times 10^8$ | 2, 2, 2, 2, 2 |
| 1 | $7.2 \times 10^2$ | NT |
| 2 | 0 | NT |
| 3 | 0 | NT |
| 4 | 0 | no deaths |
| 5 | 0 | no deaths |
| 6 | 0 | no deaths |

NT = not tested

In the second set of parallel experiments, handling and sample manipulation in the T-75 tissue culture flasks produced greater loss of factor VIII activity than was caused by the inactivation procedure (Table 8). After 18 hours of treatment, activity in the sample containing fucoumarins and exposed to UVA was 98% of that remaining in the shielded handling control which contained no fucoumarins. These results (Table 8) demonstrated that the activity of a highly labile protein can be preserved under conditions capable of inactivating high titers of non-A, non-B hepatitis virus.

TABLE 8

| Fucoumarins/UVA (hours) | Factor VIII Activity (units/ml) | | % Activity Retained (Test/Control) × 100 |
|---|---|---|---|
| | Test | Handling Control | |
| 3 | 0.91 | 1.02 | 89 |
| 6 | 0.79 | 0.82 | 96 |
| 9 | 0.69 | 0.89 | 79 |
| 12 | 0.74 | 0.79 | 94 |
| 15 | 0.66 | 0.73 | 90 |
| 18 | 0.59 | 0.60 | 98 |

EXPERIMENT IX

Inactivation of non-A, non-B hepatitis and hepatitis B viruses in combination

Two samples, each of which contained about $10^{4.5}$ $CID_{50}$ of MS-2 (ayw) strain of hepatitis B virus (HBV) and $10^4$ $CID_{50}$ of the Hutchinson stain of non-A, non-B hepatitus virus (NANB), were prepared for inactivation. The diluent for one sample was reconstituted AHF concentrate (Factor VIII). The diluent for the other sample was phosphate-buffered saline (PBS). Each sample contained an aliquot of bacteriophage R17 as an internal control. The HBV and NANB viruses were portions of National Institutes of Health stock materials diluted in fetal calf serum (FCS) or 1% bovine serum albumin (BSA). Heparin (1 unit/ml) was included in sample preparation to control any activated clotting factors present in the calf serum. 8-Methoxypsoralen was dissolved in dimethyl sulfoxide (DMSO) and added to each sample at final concentration of 300 micrograms per ml. The DMSO was present as 6% of the total sample volume of 5 ml.

Samples containing vesicular stomatitis virus (VSV), feline leukemia virus (FeLV), and bacteriophages fd and R17 were prepared in factor VIII diluent and inactivated in parallel with the hepatitis virus samples to serve as external controls.

Experimental and control samples were mixed in 50 ml polypropylene conical vials, then pipetted gently into silanized glass medicine bottles (250 cc) prior to inactivation. Sample bottles were capped with cuffed rubber stoppers fitted with blunt cannulas. Prior to inactivation, samples were flushed with a mixture of 4% hydrogen in pre-purified nitrogen for 1 hour. The oxygen level throughout the flushing cycle was below 1 ppm of oxygen as measured by a Couloximeter (Chemical Sensor Development, Torrence, CA). Samples were irradiated at approximately 5 mW/cm². After five hours irradiation, the hepatitis samples (Nos. 5 and 6) were transferred to fresh bottles, a second aliquot of R17 was added to the hepatitis samples, and the bottles were flushed for 30 minutes with the hydrogen/nitrogen mixture. These samples were then irradiated for an additional five hours. Results of the assays for infectivity of control viruses are presented in Table 9.

TABLE 9

| Sample (virus) | Hours UVA (pfu/ml or ffu/ml) | | | | | | | |
|---|---|---|---|---|---|---|---|---|
| | 0 | 1 | 2 | 2.5 | 3 | 4 | 5 | 7.5 | 10 |
| No. 5 (R17)* | [~$10^8$] | — | — | — | — | — | 0 | — | 0 |
| No. 6 (R17)* | [~$10^8$] | — | — | — | — | — | 0 | — | 0 |

TABLE 9-continued

| Sample (virus) | Hours UVA (pfu/ml or ffu/ml) | | | | | | | |
|---|---|---|---|---|---|---|---|---|
| | 0 | 1 | 2 | 2.5 | 3 | 4 | 5 | 7.5 | 10 |
| VSV-2** | $1.83 \times 10^8$ | — | — | 0 | — | — | 0 | 0 | 0 |
| FeLV-2 | $2 \times 10^4$ | — | — | 0 | — | — | 0 | 0 | 0 |
| R17-2 | $6.1 \times 10^8$ | $2.5 \times 10^4$ | 0 | — | 0 | 0 | 0 | — | — |
| fd-2 | $6.6 \times 10^{10}$ | <10 | 0 | — | 0 | 0 | 0 | — | — |

*Safety tests for endotoxin were performed by injecting 0.2 ml crude R17 filtrate into the ear vein of one rabbit and 0.2 ml of $10^{-2}$ dilution into the ear vein of another rabbit. No reactions were seen during the two-week observation period following the injection.
**An aliquot of this sample inactivated for 10 hours was tested by suckling mouse brain assay for residual infectivity. 10 suckling mice <14 days old were injected intracerebrally with 20 μl of the VSV sample. Two died of trauma, while the remaining 8 were alive and well at 14 days.

As seen in Table 9, the internal control virus (R17), a single stranded RNA bacteriophage, was completely inactivated in both samples No. 5 and No. 6 at the 5 hour time point. Initial titer was $10^8$ pfu/ml. A second aliquot containing $10^8$ pfu/ml was added at five hours. After 10 hours this second aliquot was also completely inactivated.

Parallel samples containing factor VIII concentrate were prepared and irradiated as described above. Results are shown in Table 10. No loss of factor VIII activity was observed after 10 hours of treatment.

TABLE 10

| | Sample | |
|---|---|---|
| | No. 1 | No. 2 |
| 8-MOP | 0 | 0.06 ml (300 μg) |
| UVA (hours) | 0 | 10 |
| Barbital Buffer | 0.06 ml | 0 |
| Koate | 0.84 ml | 0.84 |
| R-17/fd* | 0.10 | 0.10 |
| Viral activity (pfu/ml) | $1.2 \times 10^{10}$ | 0 |
| Factor VIII activity units/ml | 19.4 | 19.4 |

*Virus prepared as 1:10 dilution in 5% BSA

At Southwest Foundation for Biomedical Research, chimp No. 64 was inoculated with sample No. 5 and chimp No. 216 was inoculated with sample No. 6. These chimps had been on baseline evaluation for several months and had no elevations in liver enzymes on weekly testing. The animals were bled weekly, and the samples were tested for SGPT, SGOT, and HBsAg, anti-Hbs and anti-HBc. Liver biopsies were obtained at weeks 5, 7, 9, 11, 13, 15, 20, and 26. Biopsy material was examined by light microscopy immunofluorescence and electron microscopy for changes characteristic of hepatitis infection. During the 26-week observation period following inoculation, enzyme levels remained low, histology examinations were normal, and no HBV markers were detected.

EXPERIMENT X

Inactivation of Simian AIDS (SAIDS) Virus (an RNA virus) with AMT.

Vacutainer tubes (10 cc) were prepared with 0.5 ml of the fresh sterile solutions indicated in Table 11 and stored overnight at 4° C. 0.5 ml of SAIDS virus suspension was added sterilely to each tube. Samples were irradiated with approximately 5 mW/cm² UVA for the times indicated in Table 11. Non-irradiated samples were stored in the dark at 4° C. All samples were added to Raji cells and observed fior syncytia induction over a 10 day period. Cultures were then expanded and observed for an additional 10 days. Samples that had been positive (1, 3, 5, 8, 9) were expanded into flasks and supernatants from the flasks were filtered through a 0.45 μm filter. The filtrates were added to fresh Raji cells and observed for syncytia induction.

Results are shown in Table 11. The initial syncytial induction in samples 1, 8 and 9 may have been due to the presence of inactivated virus. The only samples which remained positive after expansion were the ones which received no UVA treatment (samples 3, 5, 9 and the untreated control).

TABLE 11

| Sample | AMT 1* | Ascorbate 1** | PBS-A 1 | UVA | Syncytia Initial | Formation Subculture |
|---|---|---|---|---|---|---|
| 1 | — | 50 | 450 | 2 hr | + | — |
| 2 | 20 | — | 480 | 2 hr | — | — |
| 3 | — | — | 500 | — | + | + |
| 4 | — | — | 500 | 2 hr | — | — |
| 5 | 20 | 50 | 430 | — | + | + |
| 6 | 20 | 50 | 430 | 15 min | — | — |
| 7 | 20 | 50 | 430 | 30 min | — | — |
| 8 | 20 | 50 | 430 | 1 hr | + | — |
| 9 | 20 | 50 | 430 | 2 hr | + | — |
| untreated | — | — | — | — | + | + |

*AMT, 5 mg/ml in dH$_2$O (filter sterilized)
**Sodium ascorbate, 200 mM in dH$_2$O (filter sterilized)

EXPERIMENT XI

Inactivation of Feline Leukemia Virus (FeLV-A) (an RNA virus) with 8-MOP in DMSO.

Two-ml aliquots of FeLV-A at $2 \times 10^7$ FFU/ml in F-12K medium were placed in vacutainer tubes. 8-MOP was dissolved in DMSO and added to the virus-containing samples to a final concentration of 50 μg/ml as shown in Table 14. All samples were flushed with argon for 30 min. Irradiated samples were exposed to UVA at approximately 4 mW/cm$^2$ for the times shown in Table 14. The unirradiated controls were stored in the dark at 4° C. The two 25-hour samples received additions of 8-MOP at 0, 5, 10, 15 and 20 hours. After each addition the tubes were flushed with argon for 30 min. Assessment of inactivation was by Clone 81 focus assay for all samples and blind passage on AK-D cells for 6 weeks for sample H.

Results of the focus assays are given in Table 12. No live virus was detected in any of the experimental samples following 2 hr UVA irradiation.

TABLE 12

| Sample | 8-MOP μg/ml | UVA (hrs) | Tube Changes | Cl-81 Focus Assay Titer (FFU/ml) |
|---|---|---|---|---|
| A | 0 | 0 | 3 | $1.71 \times 10^7$ |
| B | 0 | 25 | 3 | $6.45 \times 10^6$ |
| C | 250* | 0 | 3 | $1.8 \times 10^7$ |
| D | 50 | 1 | 0 | $7.71 \times 10^2$ |
| E | 50 | 2 | 0 | 0 |
| F | 50 | 4 | 0 | 0 |
| G | 50 | 6 | 0 | 0 |
| H | 250* | 25 | 3 | 0 |

*(50 μg/ml) × 5 additions

EXPERIMENT XII

Effect of Oxygen Levels on Factor VIII Exposed to Furocoumarins and UVA

THe following experiment was conducted to determine the effect of different levels of molecular oxygen on factor VIII exposed to furocoumarins and UVA light.

Furocoumarins used for this experiment were 8-methoxypsoralen (8-MOP) and 4'-aminomethyl-4',5',8-trimethylpsoralen (AMT). Samples of factor VIII concentrate (Koate, Cutter Biological) were flushed with gas containing various levels of molecular oxygen for a time sufficient to reach equilibrium ($\geq 1$ hour). The samples were contained in 10 ml red-top vacutainer tubes (Becton-Dickinson). 8-MOP or AMT was added to give a final concentration of 0.2 mM furocoumarin (8-MOP: 43.2 μg/ml; AMT: 58.6 μg/ml). Total sample volume was 1.0 ml. The sample tubes were irradiated at approximately 2.5 mW/cm$^2$ for 10 hours. Results of factor VIII assays are given in Table 13.

TABLE 13

| Oxygen level (parts per million) | Factor VIII Activity (units/ml) | | |
|---|---|---|---|
|  | 8-MOP and UVA | AMT and UVA | Control no UVA |
| 1 | 20.4 | 20.0 | — |
| 54 | 15.2 | 8.8 | — |
| 988 | 10.0 | 5.3 | 18.8* |
| 210,000 (Room air) | 3.4 | 0.3 | 20.0** |

*8-MOP added, flushed
**no drug, no flushing

Decreasing the oxygen level has a protective effect on factor VIII exposed to furocoumarin and UVA light. There was no discernible loss of factor VIII activity at the lowest level of oxygen used (approx. 1 ppm). This oxygen effect was seen for both 8-MOP and for AMT, although the loss of factor VIII activity at the higher levels of oxygen was more marked for AMT. This is much more active on a molar basis than 8-MOP as a singlet oxygen generator.

It is evident from the above results, and in accordance with the subject invention, that polynucleotides in biochemical compositions can be inactivated to provide a safe composition for administration to a mammalian host. The proteins present in the composition retain their physiological activity, so that they can fulfill their physiological function in a mammalian host. The method is simple, rapid, and can be expanded to treat large samples. The small amount of chemical reagent required will not generally be harmful to the host.

Although the foregoing invention has been described in some detail by way of illustration and example for purposes of clarity of understanding, it will be obvious that certain changes and modifications may be practiced within the scope of the appended claims.

What is claimed is:

1. A method for decontaminating a blood clotting factor containing composition of viral contaminants, in a manner which substantially maintains the biological activity of the blood clotting factors, said method comprising adding to the blood clotting factor containing composition at least one furocoumarin, and irradiating the furocoumarin containing composition under U-V light, wherein the amount of furocoumarin and irradiation conditions are sufficient to inactivate substantially all the viral contaminants, and wherein the concentration of dissolved oxygen is reduced to a level sufficient to substantially inhibit the denaturation of the blood clotting factors.

2. A method as in claim 1, wherein the level of dissolved oxygen is reduced by addition of an oxygen scavenger to the composition.

3. A method as in claim 1, wherein the level of dissolved oxygen is reduced by equilibrium exchange with an inert or less reactive gas.

4. A method as in claim 1, wherein the level of dissolved oxygen and other reactive species is reduced by addition of a physiologically-acceptable protein.

5. A method as in claim 4, wherein the physiologically acceptable protein is human or bovine serum albumin.

6. A method as in claim 1, wherein the solubility of the furocoumarin in the aqueous composition is increased by the addition of from about 1% to 25% by weight of an organic solvent.

7. A method as in claim 6, wherein the organic solvent is selected from the group consisting of dimethyl sulfoxide, ethanol, glycerol, polyethylene glycol, and propylene glycol.

8. A method according to claim 1, wherein at least two furocoumarins are present.

9. A method according to claim 1 wherein any unreacted furocoumarin(s) or photobreakdown products thereof are selectively removed.

10. A method according to claim 1 wherein furocoumarins or biological components which have reacted with the furocoumarin(s) are selectively removed by antibodies to those modified components.

11. A method for decontaminating a blood clotting factor containing composition of viral contaminants in a manner which substantially maintains the biological activity of the blood clotting factors, said method comprising adding to the blood clotting factor containing composition at least one furocoumarin such that the total furocoumarin concentration is at least 1 µg/ml and not more than 300 µg/ml, and irradiating the furocoumarin containing composition under U-V light which wavelengths are in the range of about 300 nm to 400 nm and at an intensity of about 0.1 mw/cm$^2$ to 5 w/cm$^2$ and at a depth of at least 0.025 millimeters for a total irradiation time of about 5 minutes to about 12 hours, and wherein the level of dissolved oxygen in the blood clotting factor containing composition is substantially reduced to substantially inhibit the denaturation of the blood clotting factors.

12. A method as in claim 11, wherein the level of dissolved oxygen is reduced by addition of an oxygen scavenger to the composition.

13. A method as in claim 11, wherein the level of dissolved oxygen is reduced by equilibrium exchange with a less reactive gas.

14. A method as in claim 11, wherein the level of dissolved oxygen and other reactive species is reduced by addition of a physiologically-acceptable protein.

15. A method as in claim 14, wherein the physiologically acceptable protein is human or bovine serum albumin.

16. A method as in claim 11, wherein the solubility of the furocoumarin in the aqueous composition is increased by the addition of from about 1% to 25% by weight of an organic solvent.

17. A method as in claim 16, wherein the organic solvent is selected from the group consisting of dimethyl sulfoxide, ethanol, glycerol, polyethylene glycol, and propylene glycol.

18. A method according to claim 11, wherein two furocoumarins are added to said composition.

19. A method according to claim 18, wherein said two furocoumarins are 4'-hydroxymethyl-4,5',8-trimethylpsoralen and 4'-aminomethyl-4,5',8-trimethylpsoralen.

20. A method according to claim 11, wherein the viral contaminants comprise at least one of Hepatitis A, Hepatitis B, and Non-A Non-B Hepatitis viruses.

21. A method according to claim 11 wherein the viral contaminants comprise a virus which causes Acquired Immune Deficiency Syndrome (AIDS).

22. A method according to claim 11 wherein the furocoumarin added is 8-methoxypsoralen.

* * * * *